United States Patent [19]

Hertl et al.

[11] 4,333,564

[45] Jun. 8, 1982

[54] METHOD OF CONTROLLING RHEOLOGICAL PROPERTIES OF GEL-LIKE COMPOSITIONS

[75] Inventors: William Hertl; Anthony R. Zine, Jr., both of Corning, N.Y.

[73] Assignee: Sherwood Medical Industries Inc., St. Louis, Mo.

[21] Appl. No.: 112,684

[22] Filed: Jan. 16, 1980

Related U.S. Application Data

[63] Continuation of Ser. No. 908,002, May 22, 1978, abandoned.

[51] Int. Cl.³ .................... B01D 21/26; B01J 13/00
[52] U.S. Cl. .................... 206/216; 206/219; 206/525; 210/789; 252/60; 252/316
[58] Field of Search ............ 252/60, 316; 210/789; 206/216, 525

[56] References Cited

U.S. PATENT DOCUMENTS

| | | | |
|---|---|---|---|
| 3,526,594 | 9/1970 | Meghir | 252/28 |
| 3,600,326 | 8/1971 | Wilcox et al. | 252/309 |
| 3,666,681 | 5/1972 | Keil | 252/358 |
| 3,780,935 | 12/1973 | Lukacs et al. | 233/1 A |
| 3,852,194 | 12/1974 | Zine, Jr. | 233/1 A X |
| 3,920,549 | 11/1975 | Gigliello et al. | 210/789 |
| 3,963,119 | 6/1976 | Lukacs et al. | 206/216 |
| 4,012,334 | 3/1977 | Raleigh et al. | 252/358 X |
| 4,021,340 | 5/1977 | Zine, Jr. | 210/789 |
| 4,049,692 | 9/1977 | Zine, Jr. | 233/26 X |

*Primary Examiner*—Richard D. Lovering
*Attorney, Agent, or Firm*—Stanley N. Garber; William R. O'Meara

[57] ABSTRACT

The rheological properties of thixotropic, gel-like compositions employed in blood separation tubes are controlled by incorporating in the composition up to about five percent by weight, based on the amount of composition, of a disilazane.

21 Claims, No Drawings

METHOD OF CONTROLLING RHEOLOGICAL PROPERTIES OF GEL-LIKE COMPOSITIONS

This is a continuation of application Ser. No. 908,002, filed May 22, 1978, now abandoned.

BACKGROUND OF THE INVENTION

It is well established that water-insoluble, thixotropic, gel-like compositions can be used in blood collection tubes to form a barrier between centrifuged red blood cells and the supernatant serum, thereby permitting the ready removal or isolation of the serum without contamination by the red blood cells. See, e.g., U.S. Pat. Nos. 3,780,935; 3,852,194; 3,920,549; and 4,021,340, which teach the use of silicone fluids or polybutenes (or polyisobutenes) in combination with appropriate fillers as the thixotropic, gel-like compositions which are suitable for use in such collection tubes.

Because the specific gravities of the centrifuged red blood cells and the supernatant serum are in the ranges of from about 1.092 to about 1.095 and from about 1.026 to about 1.031, respectively, the gel-like compositions employed to separate the two phases will have specific gravities of from about 1.03 to about 1.09 and preferably from about 1.037 to about 1.05. Thus, the amount of filler employed with any given liquid component is, in essence, fixed.

It should be apparent, therefore, that the rheological properties of the prior art gel-like compositions generally can be varied or controlled only by changes in the composition components. That is, for any given gel-like composition, the rheological properties of the composition are, as a practical matter, predetermined by the specific gravities of the liquid component and the filler and the viscosity of the liquid component.

Because of the nature of the interactions involved in such thixotropic, gel-like compositions, the rheological properties can be varied to some extent by employing two or more fillers having different affinities. As used herein, the term "affinity" (or variations thereof) refers to the number of hydroxy groups present on the filler surface per unit area. Because composition viscosity results largely from interactions between the liquid component and filler surface hydroxy groups, composition viscosity can be altered by changing overall or total filler affinity. Similarly, such changes affect the thixotropic index of the composition since thixotropy results largely through particle-particle interactions via filler surface hydroxy groups.

As a practical matter, however, the use of more than one filler introduces a new problem, that of "wet-out". As used herein, "wet-out" refers to the loss of composition viscosity with time, with the concomitant separation of small amounts of the liquid component. In fact, wet-out can occur with compositions prepared from a silicone fluid and a single filler, such as silica, and U.S. Pat. No. 4,049,692 is directed to preventing wet-out in this latter situation. According to the patent, wet-out is prevented by incorporating in the composition an effective amount of a polysiloxanepolyoxyalkyl copolymer which effectively increases and stabilizes composition viscosity.

There still is a need, however, for a simple, effective, and reproducible means of controlling the rheological properties of the thixotropic, gel-like compositions employed in blood separation tubes, particularly when composition viscosities or thixotropic indices are too high.

It should be noted that the separate treatment of a filler, e.g. silica, with a disilazane, e.g. hexamethyldisilazane, does not constitute a part of the present invention. More specifically, the treatment of silica with hexamethyldisilazane is known. For example, U.S. Pat. No. 3,600,326 discloses the preparation of hydrophobic silica by milling a mixture of colloidal silica, Skellysolve F, and hexamethyldisilazane and then flashing off the solvent. Furthermore, the kinetics of the reaction of hexamethyldisilazane with the hydroxy groups on the surface of silica have been studied; see M. L. Hair et al., *J. Phsy. Chem.*, 75, 2181 (1971) [*Chem. Abstr.*, 75, 67966m (1971)].

It also should be noted that colloidal silica which was pretreated with either hexamethyldisilazane or a fluorosilane has been employed to prepare a silicone fluid-based lubricating grease. See U.S. Pat. No. 3,526,594. Such pretreated silica also is known to be useful in chromatography.

These prior art procedures all involve the pretreatment of silica. The references do not disclose or suggest the in situ use of a disilazane to modify a filler having surface hydroxy groups in order to control the rheological properties of a water-insoluble, thixotropic, gel-like composition which is suitable for use in blood collection tubes.

SUMMARY OF THE INVENTION

Accordingly, the present invention provides a method of controlling the rheological properties of water-insoluble, thixotropic, gel-like compositions employed in blood separation tubes which comprises the steps of:

A. mixing a liquid component and an inert, finely-divided filler having a density greater than about 1.03 to give a water-insoluble, thixotropic, gel-like composition having a density of from about 1.03 to about 1.09;

B. reacting with the resulting composition an amount of a disilazane sufficient to reduce the composition viscosity or thixotropic index to a desired level; and C. subjecting the resulting treated composition to reduced pressure for a time sufficient to remove ammonia formed in step B and any dissolved air which may be present; wherein the disilazane has the general formula,

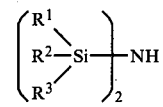

in which $R^1$, $R^2$, and $R^3$ independently are selected from the group consisting of hydrogen, $C_1$-$C_{18}$ alkyl, and $C_2$-$C_4$ alkenyl, with the proviso that no more than one of $R^1$, $R^2$, and $R^3$ can contain more than three carbon atoms.

The present invention also provides an improvement in a water-insoluble, thixotropic, gel-like composition having a specific gravity of from about 1.03 to about 1.09, which is suitable for use in blood separation tubes, and which comprises a liquid component and an inert, finely-divided filler having a density greater than about 1.03, the improvement which comprises incorporating in the composition an amount of a disilazane sufficient to reduce the composition viscosity or thixotropic index to a desired level, wherein the disilazane has the general formula given above.

DETAILED DESCRIPTION OF THE INVENTION

The first step in the method of the present invention comprises mixing a liquid component and an inert, finely-divided filler having a density greater than about 1.03 to give a water-insoluble, thixotropic, gel-like composition having a density of from about 1.03 to about 1.09.

In general, mixing can be carried out by any known means at any temperature which is not detrimental to the liquid component. As a practical matter, mixing normally will be carried out at a temperature of from about 0° C. to about 200° C. Preferably, mixing will be carried out at ambient temperature.

The liquid component generally can be any of the known materials which include silicone fluids, polybutenes, polyisobutenes, mineral oils, polyesters, liquid polymers of butadiene which contain at least 50% by weight of butadiene and up to 50% by weight of one or more ethylenically-unsaturated monomers such as styrene and which are described in copending and commonly-assigned application Ser. No. 881,251, filed Feb. 27, 1978, and now abandoned, in the names of W. Hertl and A. R. Zine, and the like.

Similarly, the inert, finely-divided filler can be any of the known fillers which have surface hydroxy groups. Examples of such fillers include, among others, such siliceous and nonsiliceous materials as glass, silica, mica, alumina, magnesia, titania, and the like. Siliceous materials are preferred, with silica being more preferred. Most preferably, the silica will have a surface area of at least about 30 m²/g.

The resulting gel-like composition typically has a viscosity of about 2,000,000 cs. If desired or necessary, the composition can be passed one or more times through a three-roll mill or similar apparatus to break up any large agglomerates of filler which may be present. A second optional treatment, which is desirable and preferred when the filler is hygroscopic, e.g. silica, consists of stirring and heating the composition under reduced pressure for a time sufficient to remove water introduced with the filler. Heating typically is in the range of from about 100° C. to about 200° C., with 130° C. being a preferred temperature.

The second step in the disclosed method comprises reacting the composition resulting from the first step with an amount of a disilazane sufficient to reduce the composition viscosity or thixotropic index to a desired level. The disilazane has the general formula,

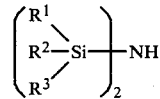

in which $R^1$, $R^2$, and $R^3$ independently are selected from the group consisting of hydrogen, $C_1$–$C_{18}$ alkyl, and $C_2$–$C_4$ alkenyl, with the proviso that no more than one of $R^1$, $R^2$, and $R^3$ can contain more than three carbon atoms.

As used herein, the term "$C_1$–$C_{18}$ alkyl" includes, among others, such groups as methyl, ethyl, propyl, isopropyl, butyl, isobutyl, sec-butyl, t-butyl, pentyl, 1,2-dimethylpropyl, hexyl, neohexyl, 2-ethylbutyl, heptyl, octyl, isooctyl, 1,3,5-trimethylpentyl, nonyl, 2-ethyl-3-methylhexyl, decyl, undecyl, 4-isopropyl-2-methylheptyl, dodecyl, neododecyl, tridecyl, tetradecyl, 6-ethyl-3,7-dimethylnonyl, pentadecyl, hexadecyl, 3-propyltridecyl, heptadecyl, octadecyl, 2,5-diethyl-2,6,8-trimethylundecyl, and the like.

As used herein, the term "$C_2$–$C_4$ alkenyl" is meant to include, among others, such groups as vinyl, allyl, methallyl, 1-propenyl, isopropenyl, 1-butenyl, 2-butenyl, 3-butenyl, and the like.

Preferably, $R^1$, $R^2$, and $R^3$ independently are selected from the group consisting of $C_1$–$C_3$ alkyl, i.e., methyl, ethyl, propyl, and isopropyl. Most preferably, each of $R^1$, $R^2$, and $R^3$ is methyl.

By way of illustration only, examples of suitable disilazanes include, among others, hexamethyldisilazane, hexaethyldisilazane, tetramethyldipropyldisilazane, tetraethyldihexyldisilazane, diethyldiisopropyldimethyldisilazane, tetramethyldioctyldisilazane, tetramethyldioctadecyldisilazane, tetramethyldivinyldisilazane, and the like. The most preferred disilazane, of course, is hexamethyldisilazane.

The disilazanes are prepared by methods well known in the art. For example, treatment of the appropriately-substituted silyl chloride in anhydrous diethyl ether at 0°–7° C. with ammonia yields the corresponding disilazane. M. F. Shostakovaskii et al., *Zhur. Obshchei Khim.*, 24, 2202 (1954) [*Chem. Abstr.* 50, 162c (1956)]. Alternatively, the silyl chloride can be treated with liquid ammonia at superatmospheric pressure, at a temperature of 15°–150° C. and in an inert solvent such as hexane. British Patent Specification No. 737,229. Disilazanes also can be prepared from the disiloxanes by converting a disiloxane to the disilyl sulfate with concentrated sulfuric acid, and then treating the sulfate, dissolved in diethyl ether, with anhydrous ammonia. L. H. Sommer et al., *J. Am. Chem. Soc.*, 70, 445 (1948). For other preparative procedures, see C. R. Hauser and C. R. Hance, *J. Am. Chem. Soc.* 73, 5846 (1951); C. R. Hauser and C. R. Hance, *J. Am. Chem. Soc.*, 74, 5091 (1952); J. F. Hyde et al., *J. Am. Chem. Soc.*, 75, 5615 (1953); and K. Ruehlmann, Angew, *Chem.*, 74, 468 (1962) [*Chem. Abstr.*, 59, 5188e (1963)].

The reaction of the disilazane with the composition from the first step can be carried out at any temperature at which the composition and the disilazane are stable. Typically, the reaction will be carried out at a temperature of from about 0° C. to about 200° C. Preferably, the reaction will be carried out at ambient temperature. Reaction time is not critical, but is dependent in part upon the reaction temperature. Thus, reaction times can vary from several minutes or less to an hour or more. At ambient temperature, a reaction time of about ten minutes is sufficient. At higher temperatures, shorter reaction times should suffice. It should be noted that other factors which can affect the reaction time include the composition viscosity and the type of equipment employed.

The amount of disilazane employed depends upon the viscosity of the composition obtained in the first step and the final viscosity or thixotropic index desired. The disilazane will decrease both the viscosity and the thixotropic index of the untreated composition. The thixotropic index, however, is in part a function of the viscosity of the liquid component of the gel-like composition obtained in the first step. Typically, amounts of disilazane in excess of about five percent by weight of the gel-like composition are not required, although larger amounts can be used, if desired.

The third step of the method of the present invention comprises subjecting the treated composition to reduced pressure for a time sufficient to remove ammonia formed in the second step and any dissolved air which may be present. This step can be carried out at any convenient temperature which is not detrimental to the treated composition. In general, however, the temperature will be in the range of from about 0° C. to about 200° C. A convenient temperature has been found to be about 130° C. The time of the reduced pressure treatment is not critical and can vary from several minutes or less to several hours or more.

The degree of pressure reduction also is not critical. Preferably, however, the pressure will be reduced to below about 100 mm. Hg, and most preferably below about 75 mm. Hg. An approximately 30-minute treatment period has been found to be sufficient at a temperature of about 130° C. and a pressure below about 10 mm. Hg to permit the removal of all ammonia and dissolved air.

The present invention is further described, but not limited, by the examples which follow. Example 1 illustrates the effects of the amount of disilazane on composition viscosity and thixotropic index. Examples 2–5, inclusive, illustrate that the composition thixotropic index can be controlled at constant disilazane levels by varying the viscosity of the liquid component of the composition.

EXAMPLE 1

Varying levels of hexamethyldisilazane (HMDS) were added to a series of gel-like compositions. In each case, the composition comprised 100 g. of H-100 polyisobutylene (marketed by Amoco Chemicals Corporation, Chicago, Ill., and described in that company's Bulletin 12-H as a butylene polymer composed predominantly of high molecular weight mono-olefins, i.e. 85–95%., the remainder being isoparaffins), and 33 g. of OX-50, a fumed silica powder having a surface area of 30–50 m²/g. (Degussa, Inc., Pigments Division, New York, N.Y.); the viscosity of the H-100 polymer was 26,000 centistokes. The composition viscosities and thixotropic indices are summarized in Table I (each composition had a density of 1.04).

TABLE I

Properties of H-100/OX-50 Gel-like Compositions Having Densities of 1.04 and Containing Varying Amounts of HMDS

| Example | % HMDS | Viscosity (cs) | Thixotropic Index |
|---------|--------|----------------|-------------------|
| 1a | 0 | 1,820,000 | 7.6 |
| 1b | 0.01 | 1,780,000 | 7.3 |
| 1c | 0.05 | 946,000 | 4.9 |
| 1d | 0.10 | 855,000 | 4.2 |
| 1e | 0.30 | 546,000 | 3.6 |
| 1f | 0.40 | 455,000 | 3.2 |
| 1g | 0.50 | 364,000 | 2.4 |
| 1h | 0.60 | 345,000 | 2.4 |
| 1i | 5.0 | 280,000 | 1.9 |

EXAMPLES 2–5

A series of gel-like compositions was formulated with different polyisobutylene polymers and different amounts of OX-50 filler. Each composition contained 5% HMDS. The compositions per se are summarized in Table II and the properties of the compositions are summarized in Table III.

TABLE II

Thixotropic Compositions Comprising Polyisobutylene Polymers and OX-50 Filler with 5% HMDS

| Example | Type | Polymer Visc. (cs) | Amt. (g) | Amt. Filler (g) |
|---------|------|--------------------|----------|-----------------|
| 2 | H-35 | 6,000 | 100 | 37 |
| 3 | H-50 | 10,000 | 100 | 34.5 |
| 4 | H-100 | 26,000 | 100 | 33 |
| 5 | H-300 | 106,000 | 100 | 30 |

TABLE III

Properties of Thixotropic Compositions Comprising Polyisobutylene Polymers and OX-50 Filler with 5% HMDS

| Example | Density | Viscosity (cs) | Thixotropic Index |
|---------|---------|----------------|-------------------|
| 2 | 1.04 | 280,000 | 4.4 |
| 3 | 1.04 | 216,000 | 3.6 |
| 4 | 1.04 | 280,000 | 2.2 |
| 5 | 1.04 | 296,000 | 1.2 |

As already indicated, the treated compositions are used in blood collection tubes to partition whole blood into a heavier portion and a lighter portion in accordance with known procedures. In general, both the treated composition and a whole blood sample are placed in a container or tube adapted to be centrifuged. The container then is centrifuged until the treated composition assumes a position at the interface between the heavier and lighter phases of the blood. Preferably, the composition initially is contained in an evacuated tube into which blood can be drawn, thus providing a closed blood-separating system. For example, the treated composition is placed in individual tubes of the type disclosed in U.S. Pat. No. 3,852,194; the tubes then are evacuated to a residual pressure of about 0.1 atm. The amount of treated composition in each 16×100 mm. tube is from about 1 to about 4 g., typically about 2 g. Each tube is capable of drawing in about 10 ml. of whole blood. In use, the tube is used to draw whole blood via a needle in the rubber stopper and the tube and its contents are then centrifuged until the thixotropic composition migrates to a position at the interface between the two phases, thereby partitioning such phases. As a practical matter, the partitioning is complete after about 10 minutes of centrifugation at 1100 RCF. After this time, the stopper can be removed and the lighter phase readily removed without disturbing the partitioning seal.

Each of the treated compositions of Examples 2–5, inclusive, was employed to successfully partition a sample of whole blood into a heavier phase and a lighter phase. In each case, the blood sample was centrifuged at 1100 RCF for ten minutes in the presence of about 2 g. of each treated composition which previously had been placed in a 16×100 mm. tube which was stoppered and evacuated to a residual pressure of 0.1 atm.

The examples clearly illustrate that composition viscosities and thixotropic indices can be controlled by the appropriate choice of liquid component viscosity and the amount of disilazane employed. In practice, it has been found that composition viscosities greater than about 300,000 cs are preferred to eliminate slumping of the seal after centrifugation, and viscosities less than about 1,300,000 cs. are preferred to allow proper movement of the composition within the tube during centrifugation. The present invention eliminates any pretreatment of the filler and, hence, avoids problems associated with filler pretreatments or mixtures. Furthermore, the present invention permits precise control of composition properties to an extent or degree not possible with pretreated fillers.

What is claimed is:

1. A method of making a gel-like material for use in a blood collection tube adapted to be centrifuged for centrifugally separating and partitioning blood phases of a blood sample introduced into the blood collection tube, comprising the steps of:

A. preparing a water insoluble, thixotropic, gel-like composition employed in blood separation tubes and controlling the rheological properties thereof including the steps of:

1. mixing a liquid component and an inert, finely-divided filler having a density greater than about 1.03 to give a gel-like composition having a density of from about 1.03 to about 1.09, said liquid component includes a material selected from the group consisting of silicone, polyisobutene, mineral oil, polyester, and liquid polymer of butadiene, said filler includes a material selected from the group consisting of glass, silica, mica, alumina, magnesia, and titania;

2. reacting with the resulting composition an amount of a disilazane sufficient to reduce the composition viscosity or thixotropic index to a desired level; and 3. subjecting the resulting treated composition to reduced pressure for a time sufficient to remove ammonia formed in step 2 and any dissolved air which may be present; wherein the disilazane has the general formula,

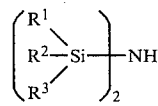

in which $R^1$, $R^2$, and $R^3$ independently are selected from the group consisting of hydrogen, $C_1$–$C_{18}$ alkyl, and $C_2$–$C_4$ alkenyl, with the proviso that more than one of $R^1$, $R^2$, and $R^3$ can contain no more than three carbon atoms, and B. introducing a quantity of the composition resulting from step 3 into a blood collection tube.

2. The method of claim 1 in which the filler has a surface area of at least about 30 m²/g.

3. The method of claim 1 in which step 1 is carried out at a temperature of from about 0° C. to about 200° C.

4. The method of claim 1 in which step 1 is carried out at ambient temperature.

5. The method of claim 1 in which $R^1$, $R^2$, and $R^3$ independently are selected from the group consisting of $C_1$–$C_3$ alkyl.

6. The method of claim 5 in which each of $R^1$, $R^2$, and $R^3$ is methyl.

7. The method of claim 1 in which the amount of disilazane is no more than about five percent by weight of the gel-like composition.

8. The method of claim 7 in which step 2 is carried out at ambient temperature.

9. The method of claim 1 in which step 2 is carried out at a temperature of from about 0° C. to about 200° C.

10. The method of claim 1 in which step 3 is carried out at a temperature of from about 0° C. to about 200° C.

11. The method of claim 10 in which step 3 is carried out at a temperature of about 130° C.

12. The method of claim 11 in which step 3 is carried out for a period of about 30 minutes.

13. The method of claim 1 in which step 3 is carried out at a pressure below about 100 mm. Hg.

14. In a water-insoluble, thixotropic, gel-like composition having a specific gravity of from about 1.03 to about 1.09, suitable for use in blood separation tubes, which comprises a liquid component including a material selected from the group consisting of polybutene, polybutadiene, and butadiene-styrene copolymer, and an inert, finely-divided filler having a density greater than about 1.03 and selected from the group consisting of glass, silica, mica, alumina, magnesia, and titania, the improvement which comprises incorporating in the composition an amount of a disilazane sufficient to reduce the composition viscosity or thixotropic index to the desired level, wherein the disilazane has the general formula,

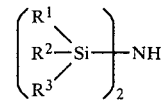

in which $R^1$, $R^2$, and $R^3$ independently are selected from the group consisting of hydrogen, $C_1$–$C_{18}$ alkyl, and $C_2$–$C_4$ alkenyl, with the proviso that no more than one of $R^1$, $R^2$, and $R^3$ can contain more than three carbon atoms.

15. In combination, a blood separation tube, a water-insoluble, thixotropic, gel-like composition having a specific gravity of from about 1.03 to about 1.09, disposed in said blood separation tube, said composition comprising a liquid component including a material selected from the group consisting of silicone, mineral oil, polyester, butadiene polymer, and butylene polymer, and an inert, finely-divided filler including a material selected from the group consisting of glass, silica, mica, alumina, magnesia, and titania and having a density greater than about 1.03, a disilazane incorporated into said composition in an amount sufficient to reduce the composition viscosity or thixotropic index to the desired level, wherein the disilazane has the general formula,

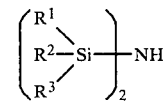

in which $R^1$, $R^2$, and $R^3$ independently are selected from the group consisting of hydrogen, $C_1$–$C_{18}$ alkyl, and $C_2$–$C_4$ alkenyl, with the proviso that no more than one of $R^1$, $R^2$, and $R^3$ can contain more than three carbon atoms.

16. The combination of claim 15 in which the liquid component is a butylene polymer.

17. The combination of claim 15 in which the liquid component is a polybutadiene.

18. The combination of claim 15 in which the liquid component is a butadiene-styrene copolymer.

19. The combination of claim 15 in which the filler is silica.

20. The combination of claim 15 in which $R^1$, $R^2$, and $R^3$ independently are selected from the group consisting of $C_1$–$C_3$ alkyl.

21. The combination of claim 20 in which each of $R^1$, $R^2$, and $R^3$ is methyl.

* * * * *